(12) United States Patent
Lan et al.

(10) Patent No.: US 11,542,426 B2
(45) Date of Patent: *Jan. 3, 2023

(54) AMIDODIAMINE CORROSION INHIBITORS

(71) Applicant: Halliburton Energy Services, Inc., Houston, TX (US)

(72) Inventors: Qiang Lan, The Woodlands, TX (US); Nathan Darrell Davis, Conroe, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 30 days.

This patent is subject to a terminal disclaimer.

(21) Appl. No.: 16/642,278

(22) PCT Filed: Sep. 29, 2017

(86) PCT No.: PCT/US2017/054367
§ 371 (c)(1),
(2) Date: Feb. 26, 2020

(87) PCT Pub. No.: WO2019/066911
PCT Pub. Date: Apr. 4, 2019

(65) Prior Publication Data
US 2021/0079290 A1 Mar. 18, 2021

(51) Int. Cl.
*C09K 8/54* (2006.01)
*C07C 53/10* (2006.01)
(Continued)

(52) U.S. Cl.
CPC ............... *C09K 8/54* (2013.01); *C07C 53/10* (2013.01); *C07C 237/10* (2013.01);
(Continued)

(58) Field of Classification Search
CPC ...... C09K 8/54; C09K 2208/32; C07C 53/10; C07C 237/10; C23F 11/141; C23F 11/145; E21B 37/06
See application file for complete search history.

(56) References Cited

U.S. PATENT DOCUMENTS 5,322,630 A 6/1994 Williams et al.
7,867,953 B2 * 1/2011 Miller ..................... C01B 33/44
507/245

(Continued)

FOREIGN PATENT DOCUMENTS

WO 2012/063055 A1 5/2012
WO WO-2016003446 A1 * 1/2016 ............. E21B 21/08
(Continued)

OTHER PUBLICATIONS

"Synthesis of Quaternary Long Chain N Alkyl Amides and Their Corrosion Inhibition in Acidic Media" Serkan Ozturk; Ayhan Yildrum; Mehmet Cetin; Mustafa Tavash J Surfact. Deterg. (2w014) 17:471-481 (Year: 2014).*
(Continued)

*Primary Examiner* — Pamela H Weiss
(74) *Attorney, Agent, or Firm* — Thomas Rooney; C. Tumey Law Group PLLC

(57) ABSTRACT

Methods for providing corrosion inhibition in conduits, containers, and wellbores penetrating subterranean formations are provided. In some embodiments, the methods comprise contacting a metal surface with a fluid comprising a corrosion inhibitor additive. In certain embodiments, the corrosion inhibitor additive comprises a compound comprising a hydrophobic cation moiety, one or more lipophilic tails, and a linking moiety.

19 Claims, 5 Drawing Sheets

(51) Int. Cl.
  *C07C 237/10* (2006.01)
  *C23F 11/14* (2006.01)
  *E21B 37/06* (2006.01)
(52) U.S. Cl.
  CPC ............ *C23F 11/141* (2013.01); *E21B 37/06* (2013.01); *C09K 2208/32* (2013.01)

(56) References Cited

U.S. PATENT DOCUMENTS

| | | | |
|---|---|---|---|
| 7,867,983 B2* | 1/2011 | Liang | A61K 31/52 514/45 |
| 7,989,403 B2 | 8/2011 | Acosta et al. | |
| 10,011,756 B2* | 7/2018 | Lan | C07C 237/10 |
| 2004/0214725 A1* | 10/2004 | Moss | B01J 13/0082 507/129 |
| 2006/0013798 A1 | 1/2006 | Henry et al. | |
| 2011/0100630 A1* | 5/2011 | Evans | C09K 8/54 166/305.1 |
| 2012/0114523 A1 | 5/2012 | Hellberg et al. | |
| 2014/0091262 A1 | 4/2014 | Webber et al. | |
| 2017/0190952 A1 | 7/2017 | Qu et al. | |
| 2018/0155607 A1* | 6/2018 | Lan | C09K 8/52 |
| 2018/0155608 A1* | 6/2018 | Lan | C09K 8/52 |

FOREIGN PATENT DOCUMENTS

| | | | | |
|---|---|---|---|---|
| WO | 2017/132306 A1 | 8/2017 | | |
| WO | WO-2017184115 A1 * | 10/2017 | ............... | C09K 8/52 |

OTHER PUBLICATIONS

International Preliminary Report on Patentability issued in related PCT Application No. PCT/US2017/054367 dated Apr. 9, 2020, 6 pages.
Examination Report issued in related Canadian Patent Application No. 3,071,507 dated May 18, 2021, 3 pages.
Search Report issued in related Brazilian Patent Application No. BR112020001253-0 completed Aug. 3, 2021, 4 pages.
International Search Report and Written Opinion issued in related PCT Application No. PCT/US2017/054367 dated Jun. 8, 2018, 10 pages.
Abstract No. 1990:162781 by Chemical Abstract Services (CAS), 1990, Maniu et al., "Selection of corrosion inhibiting agents with maximum efficiency by the EVOP (evolutive operation) technique", Industria Usoara (2989, vol. 36, No. 6, pp. 264-272.
Abstract No. 1987:485987 by Chemical Abstract Services (CAS), 1987, Landauer et al., "Corrosion inhibition effect of some quaternary ammonium salts in hydrochloric acid solutions", Bulletinul Institutului Politehnic Buchresti, Seria Chimie (1985), Volume Date 1984, pp. 46-47.

* cited by examiner

US 11,542,426 B2

AMIDODIAMINE CORROSION INHIBITORS

CROSS-REFERENCE TO RELATED APPLICATION

The present application is a U.S. National Stage Application of International Application No. PCT/US2017/054367 filed Sep. 29, 2017, which is incorporated herein by reference in its entirety for all purposes.

BACKGROUND

The present disclosure relates to compositions, treatment fluids, and methods for providing corrosion inhibition in subterranean operations, pipelines, and other related operations. The corrosion of metal surfaces occurs when metal surfaces are contacted by a corrosive environment containing an oxidizer (e.g., an electrochemical oxidizer, a chemical oxidizer or the like). Illustrative corrosive environments include, for example, acidic environments, environments containing water vapor in the presence of air and/or oxygen, and environments containing chloride or bromide ions, carbon dioxide and/or hydrogen sulfide. As used herein, the term "corrosion" refers to any reaction between a material and its environment that causes some deterioration of the material or its properties. Examples of common types of corrosion include, but are not limited to, the rusting of a metal, the dissolution of a metal in acids, and patina development on the surface of a metal.

Corrosive environments can be produced by treatment fluids that are commonly used in a number of operations in the oil and chemical industries. In such operations, any metal surfaces present (e.g., piping, tubular goods, heat exchangers and reactors) are subjected to the corrosive environment of the treatment fluid. In subterranean applications, metal surfaces on various types of equipment are often exposed to corrosive conditions during downhole operations. For example, corrosive components including brine, carbon dioxide and/or hydrogen sulfide are commonly encountered downhole. Pipelines and conduits used to transport fluids between various locations (in the oilfield industry and elsewhere) also may be exposed to fluids that can cause corrosion.

To combat potential corrosion problems, certain corrosion inhibitors have been used to reduce, inhibit, and/or substantially prevent corrosion of metal and metal alloy surfaces on downhole equipment, all with varying levels of success. As used herein, the term "inhibit" and its derivatives refer to a lessening of the tendency of a phenomenon to occur and/or the degree to which that phenomenon occurs. The term "inhibit" does not imply any particular degree or amount of inhibition.

BRIEF DESCRIPTION OF THE DRAWINGS

These drawings illustrate certain aspects of some of the embodiments of the present disclosure and should not be used to limit or define the claims.

Figure 1:
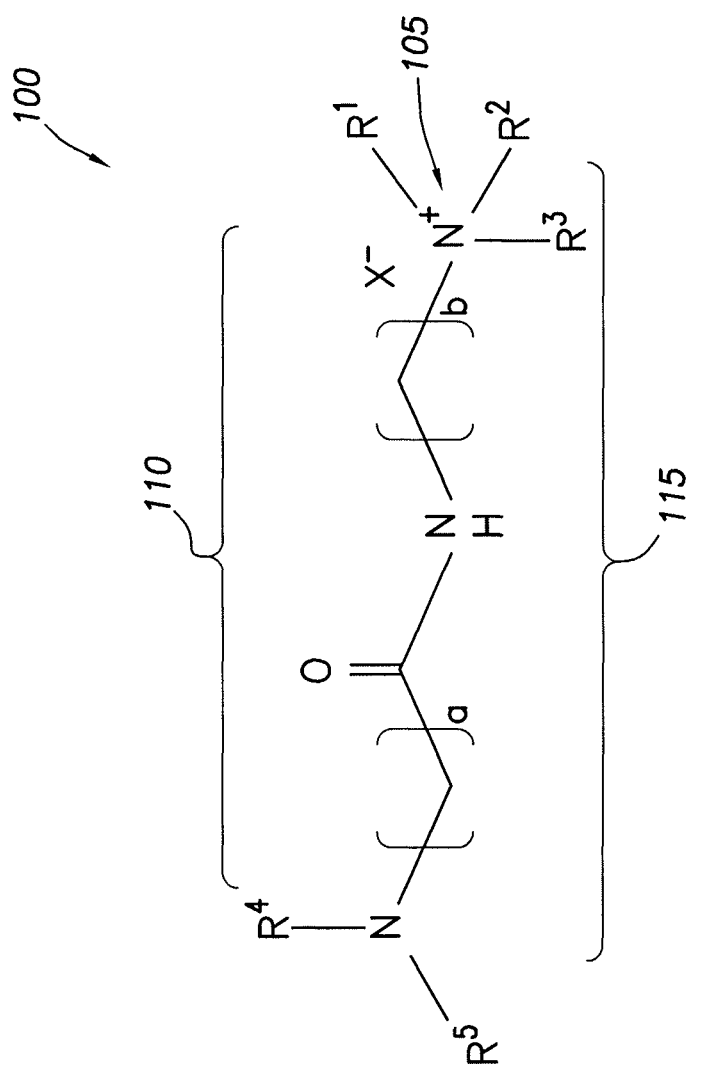
FIG. 1 is a diagram illustrating a corrosion inhibitor additive in accordance with certain embodiments of the present disclosure.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure involving wellbores may be applicable to horizontal, vertical, deviated, or otherwise nonlinear wellbores in any type of subterranean formation. Embodiments may be applicable to injection wells, monitoring wells, and production wells, including hydrocarbon or geothermal wells.

As used herein, the nomenclature "$C_x$ to $C_y$" refers to the number of carbon atoms in a hydrocarbyl group (here, ranging from x to y carbon atoms), wherein x and y may be any positive integer. As used herein, a "hydrocarbyl group" may, unless otherwise specifically noted, be branched, unbranched, non-cyclic, and/or cyclic; substituted or unsubstituted (that is, it may or may not contain one or more additional moieties or functional groups in place of one or more hydrogen atoms in the hydrocarbon chain); saturated or unsaturated; and/or may include one or more heteroatoms (e.g., O, N, P, S). As used herein, "independently" refers to the notion that preceding items may be the same as or different from each other.

The present disclosure relates to methods, systems, and compositions for providing corrosion inhibition in wellbores penetrating subterranean formations or conduits, such as pipes used for the production and/or transport of petroleum products, natural gas, and the like. In certain embodiments, the present disclosure may provide corrosion inhibitor additives including one or more lipophilic tails, a hydrophilic head, and a linking moiety. In some embodiments, the corrosion inhibitor additives may be provided, used, and/or introduced as a salt. The methods of the present disclosure may include contacting a metal surface with a fluid including a corrosion inhibitor additive, wherein the corrosion inhibitor additive includes at least one compound having the structural formula:

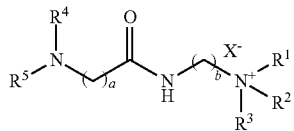

wherein each of $R^1$, $R^2$, and $R^3$ are independently selected from the group consisting of hydrogen and any $C_1$ to $C_{16}$ hydrocarbyl group, wherein $R^4$ is selected from the group consisting of hydrogen and any $C_1$ to $C_{50}$ hydrocarbyl group, wherein $R^5$ is any $C_1$ to $C_{50}$ hydrocarbyl group, wherein $X^-$ is a counter anion, and wherein each of a and b is independently an integer from 1 to 10. In certain embodiments, a fluid including the corrosion inhibitor additive may be introduced into at least a portion of a conduit or container including a metal surface. In certain embodiments, the corrosion inhibitor additive may be introduced into a wellbore penetrating at least a portion of a subterranean formation. Among the many advantages to the corrosion inhibitor additives, such additives may, among other benefits, provide corrosion inhibition at a lower cost as compared to certain traditional corrosion inhibitor additives.

In certain embodiments, the present disclosure further provides methods of using such corrosion inhibitor additives to inhibit and/or reduce corrosion in corrosive environments. For example, the corrosion inhibitor additives may inhibit and/or reduce corrosion in acidic environments, environments containing water vapor in the presence of air and/or oxygen, and environments containing chloride or bromide ions, carbon dioxide and/or hydrogen sulfide. In certain embodiments, the corrosion inhibitor additives may provide corrosion inhibition for various types of metals, including, but not limited to carbon steel, copper, and aluminum.

In some embodiments, the corrosion inhibitor additives may be film-forming corrosion inhibitors. The corrosion inhibitor additives and/or their salts may include surface-active compounds that may form a protective film on the surface of a metal that subsequently comes in contact with a corrosive environment, thereby suppressing corrosion. The effectiveness of such a film-forming corrosion inhibitor (FFCI) may be based, at least in part, on the strength of the FFCI's adsorption or other adherence to the metal surface (or to another surface such as a ferrous scale surface like siderite, iron carbonate). In certain embodiments, corrosion inhibition effectiveness increases with the strength of adsorption. Such adsorption may, in some embodiments, form a protective layer that physically, chemically, or otherwise prevents corrosive compounds from reaching the metal or other surface to which the inhibitor has adhered. In some embodiments, the protective film or layer may be removed. For example, the protective film or layer may be removed intentionally (e.g., by an additive or fluid) or simply by the passage of time.

In certain embodiments, the corrosion inhibitor additives may include a compound having a hydrophilic head that includes a cation moiety. The cation moiety may, in some embodiments, be a quaternary ammonium cation moiety or a tertiary ammonium cation moiety. FIG. 1 illustrates the chemical structure for certain compounds that may be included in the corrosion inhibitor additives of the present disclosure. In certain embodiments, the cation moiety of the compound may be bonded to other moieties of the compound, for example, as shown with respect to the hydrophilic head 105 of the corrosion inhibitor compound 100 in FIG. 1. In certain embodiments, the cation moiety may be substantially of the composition —$R^1R^2R^3N^+$—. Each of $R^1$, $R^2$, and $R^3$ may independently include either a hydrogen atom or a $C_1$ to $C_{16}$ hydrocarbyl group. In some embodiments, at least one of $R^1$, $R^2$, and $R^3$ may include an ethoxylate. In some embodiments, at least one of $R^1$, $R^2$, and $R^3$ may include a thiol group.

In certain embodiments, $R^1$, $R^2$, and/or $R^3$ may be a hydrogen atom. In certain embodiments, only one of $R^1$, $R^2$, and $R^3$ in a particular corrosion inhibitor additive of the present disclosure may be a hydrogen atom. In those embodiments, the cation moiety is a tertiary ammonium cation moiety. In other embodiments, none of $R^1$, $R^2$, and/or $R^3$ in a particular corrosion inhibitor additive of the present disclosure is a hydrogen atom. In those embodiments, each of $R^1$, $R^2$, and $R^3$ may independently include a $C_1$ to $C_6$ hydrocarbon chain, and the cation moiety is a quaternary ammonium cation moiety. In embodiments wherein at least one of $R^1$, $R^2$, and $R^3$ includes a $C_1$ to $C_6$ hydrocarbon chain, the hydrocarbon chain may include any one or more hydrocarbon groups selected from the group consisting of: alkyl, alkenyl, alkynyl, aryl, arylalkyl, arylalkenyl, alkylaryl, alkenylaryl, and any combination thereof, for example. In some embodiments, at least one of at least one of $R^1$, $R^2$, and $R^3$ includes a heteroatom. In such embodiments, any one or more of $R^1$, $R^2$, and $R^3$ may be branched, unbranched, non-cyclic, cyclic, saturated, and/or unsaturated. In certain embodiments, each of $R^1$, $R^2$, and $R^3$ may independently include (i) as few as any one of: 1, 2, 3, 4, 5, 6, 7, 8, 9, and 10 carbon atoms, and (ii) as many as one of: 2, 3, 4, 5, 6, 7, 8, 9, and 10 carbon atoms. For example, suitable ranges of carbon atoms in each of $R^1$, $R^2$, and $R^3$ according to various embodiments include, but are not limited to 1 to 2, 1 to 3, 1 to 4, 1 to 5, 1 to 6, 1 to 7, 1 to 8, 1 to 9, 1 to 10, 2 to 4, 3 to 5, 4 to 6, 5 to 7, 6 to 8, 7 to 9, 8 to 10, and the like.

In some embodiments, any one or more of $R^1$, $R^2$, and $R^3$ may include a $C_1$ to $C_{10}$ alkyl chain. In some embodiments, any one or more of $R^1$, $R^2$, and $R^3$ may include a $C_2$ to $C_6$ alkenyl or alkynyl chain. In some embodiments, any one or more of $R^1$, $R^2$, and $R^3$ may include a $C_3$ to $C_6$ cyclic moiety. In certain embodiments, any one or more of $R^1$, $R^2$, and $R^3$ may be substituted (e.g., it may include any one or more functional groups in addition to the hydrocarbon groups described above), so long as the cation moiety remains hydrophilic. In certain embodiments, at least one of $R^1$, $R^2$, and $R^3$ may include a heteroatom (e.g., may include O, N, P, S, or another atom other than C or H), so long as the cation moiety remains hydrophilic.

The compound of the corrosion inhibitor additive may further include one or more lipophilic tails. For example, as shown in FIG. 1, the compound 100 of the corrosion inhibitor additive includes two lipophilic tails $R^4$ and $R^5$. In certain embodiments, the lipophilic tails of the compound may each independently be selected from the group consisting of a hydrocarbon and $C_1$ to $C_{50}$ hydrocarbyl group. In certain embodiments, the hydrocarbyl group of the lipophilic tail(s) may be branched or unbranched, cyclic or non-cyclic, saturated or saturated, and/or may be any one or more of alkyl, alkenyl, alkynyl, and aryl groups, and/or any combination thereof. In some embodiments, at least one of $R^4$ and $R^5$ includes a heteroatom. In certain embodiments, the lipophilic tail(s) may be substituted with any one or more functional groups, so long as such substituted functional group(s) do not alter the lipophilic and/or hydrophobic nature of the lipophilic tail(s). In certain embodiments, each of the lipophilic tails may independently include (i) as few as any one of: 1, 2, 3, 4, 5, 6, 7, 8, 9, 10, 11, 12, 13, 14, 15, 16, 17, 18, 19, and 20 carbon atoms, and (ii) as many as any one of: 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, and 50 carbon atoms. For example, suitable ranges of carbon atoms in the lipophilic tail(s) according to various embodiments include, but are not limited to 1 to 5, 3 to 5, 4 to 8, 5 to 15, 8 to 18, 12 to 16, 8 to 20, 10 to 20, 15 to 20, and the like. It will be appreciated by one of ordinary skill in the art having the benefit of the present disclosure that additional lipophilic tails could be included in the compound of the corrosion inhibitor additives (e.g., at a point along the backbone 115 of the corrosion inhibitor compound 100).

The compound of the corrosion inhibitor additive may further include a linking moiety. As used herein, "linking moiety" refers to any portion of the corrosion inhibitor compound that provides spacing between the hydrophilic head and the lipophilic tail(s). In certain embodiments, one or more lipophilic tails may be connected to the hydrophilic head via the linking moiety. For example, in the compound 100 shown in FIG. 1, lipophilic tails $R^4$ and $R^5$ are connected to hydrophilic head 105 via linking moiety 110. In certain embodiments, the linking moiety may provide sufficient spacing so that the compound maintains an overall substantially amphiphilic character.

In certain embodiments, the linking moiety may include one or more hydrocarbon chains of any length, branched or unbranched, and/or saturated or unsaturated (so long as the overall corrosion inhibitor additive maintains amphiphilic character). In some embodiments, the linking moiety may include $C_1$ to $C_{20}$ hydrocarbon chains or longer. In certain embodiments, the linking moiety may be any one or more of methyl, ethyl, propyl, butyl, pentyl, hexyl, heptyl, octyl, nonyl, decyl, and the like. In certain embodiments, the linking moiety may be substituted such that it includes any kind and any number of functional groups, so long as the corrosion inhibitor compound maintains both hydrophobic and hydrophilic portions. In such embodiments, the one or more functional groups included in the linking moiety should not adversely affect the hydrophilic nature of a hydrophilic head, nor should they adversely affect the lipophilic nature of the lipophilic tail(s). Examples of suitable functional groups that may be included in the linking moiety, the lipophilic tail(s), and/or the R-groups ($R^1$, $R^2$, $R^3$) may include any one or more of: an ester, ether, amine, sulfonamide, amide, ketone, carbonyl, isocyanate, urea, urethane, and any combination thereof, for example. In some embodiments, the one or more functional groups on the linking moiety may include any group capable of reacting with an amine.

For example, compound 100 of the corrosion inhibitor additive in FIG. 1 includes example linking moiety 110 including an amide group as well as two alkyl chains of the general formulas $C_aH_{2a}$ and $C_bH_{2b}$ on either side of the amide group. In certain embodiments, each of a and b may independently be an integer from 1 to 10. In certain embodiments, each alkyl chain in the linking moiety may include (i) as few as any one of: 1, 2, 3, 4, 5, 6, 7, 8, 9 carbon atoms, and (ii) as many as any one of: 2, 3, 4, 5, 6, 7, 8, 9, and 10 carbon atoms. In some embodiments, the two alkyl chains on either side of the amide group may be linear, unbranched alkyl chains. In some embodiments, the two alkyl chains on either side of the amide group may be saturated alkyl chains.

In certain embodiments, the corrosion inhibitor additives may be characterized as reaction products. For instance, in some embodiments, the present disclosure provides corrosion inhibitor additives that may be characterized as reaction products of: (1) a dialkylaminoalkylamine having the general formula $H_2N-(CH_2)_b-NR^1R^2$ and (2) a first intermediate formed as the reaction product of one or more unsaturated carboxylic acids or esters containing an alkene chain (e.g., acrylates) and an amine. In some embodiments, the "dialkyl" groups of the dialkylaminoalkylamine may be either the same or different, and $R^1$ and $R^2$ of the cation moiety may depend upon, among other factors, the identity of the dialkyl groups of the dialkylaminoalkylamine. The length of the "alkyl" chain (i.e., $(CH_2)_b$) of the dialkylaminoalkylamine may vary from $(CH_2)_1$ to $(CH_2)_{10}$, and the length of an alkyl chain in the linking moiety having the general formula $C_bH_{2b}$ may depend upon, among other factors, the length of the alkyl chain of the dialkylaminoalkylamine. In certain embodiments, the unsaturated carboxylic acids or esters containing an alkene chain may be an alkyl alkenoate (e.g., an alkyl methacrylate, an alkyl acrylate (for example, methyl acrylate)), an alkenoic acid (e.g., acrylic acid), and any combination thereof, for example. In certain embodiments, the length of the alkyl chain in the linking moiety having the general formula $C_aH_{2a}$ may depend upon, among other factors, the identity of the unsaturated carboxylic acid or ester.

In certain embodiments, each of $R^4$ and $R^5$ is a $C_1$ to $C_{50}$ hydrocarbyl group resulting from a reaction between an acrylate or a methacrylate and an amine, the amine being selected from the group consisting of: a synthetic primary or secondary amine selected from the group consisting of: butylamine, hexylamine, octylamine, dodecylamine, N-methyldodecylamine, N-methyloctylamine, didodecylamine, and any combination thereof; a primary or secondary fatty amine derived from one or more fatty acids selected from the group consisting of: tallow, corn oil, canola oil, coconut oil, safflower oil, sesame oil, palm oil, cottonseed oil, soybean oil, olive oil, sunflower oil, hemp oil, wheat germ oil, palm kernel oil, vegetable oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof; and any combination thereof, for example.

In certain embodiments, the amine may have one or more hydrocarbon chains each of a length from $C_1$ to $C_{50}$, and the lipophilic tails $R^4$ and $R^5$ of the corrosion inhibitor compound may depend upon, among other factors, the identity of the hydrocarbon chains. In certain embodiments, the amine may include one or more functional groups and a portion of the functional group may be included in the lipophilic tails $R^4$ and $R^5$ of the corrosion inhibitor compound. Suitable amines for reaction may include, but are not limited to any primary or secondary fatty amine derived from one or more fatty acids selected from the group consisting of: tallow, corn oil, canola oil, coconut oil, safflower oil, sesame oil, palm oil, cottonseed oil, soybean oil, olive oil, sunflower oil, hemp oil, wheat germ oil, palm kernel oil, vegetable oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof, for example. Suitable amines for reaction also may include, but are not limited to, any synthetic primary or secondary amine including, but not limited to, butylamine, amine, hexylamine, octylamine, dodecylamine, N-methyldodecylamine, N-methyloctylamine, didodecylamine, and the like, and any combination or derivative thereof, for example.

In some embodiments, the reaction product of (1) the dialkylaminoalkylamine and (2) the first intermediate may form a second intermediate that may further be reacted with (3) one or more alkylating agents. In such embodiments, $R^3$ of the cation moiety may depend upon, among other factors, the alkyl group of the alkylating agent(s). In certain embodiments, the one or more alkylating agents may be a carbonate, a carboxylate, a halide (e.g., bromide, chloride, iodide), a sulfate, an organic sulfonate, a hydroxide, a phosphate, a borate, and any combination or derivative thereof, for example. In certain embodiments, the corrosion inhibitor additive is a reaction product of a reaction between (i) an alkylating agent or an acid and (ii) a second intermediate resulting from a reaction between a dialkylaminoalkylamine and a first intermediate, the first intermediate resulting from a reaction between an acrylate or a methacrylate and an amine.

In some embodiments, the corrosion inhibitor additive may exhibit synergistic effects with a thiol-containing compound. For example, in certain embodiments, a corrosion inhibitor additive may exhibit increased corrosion inhibition in the presence of a mercaptan or other thiol-containing compound.

Figure 2:
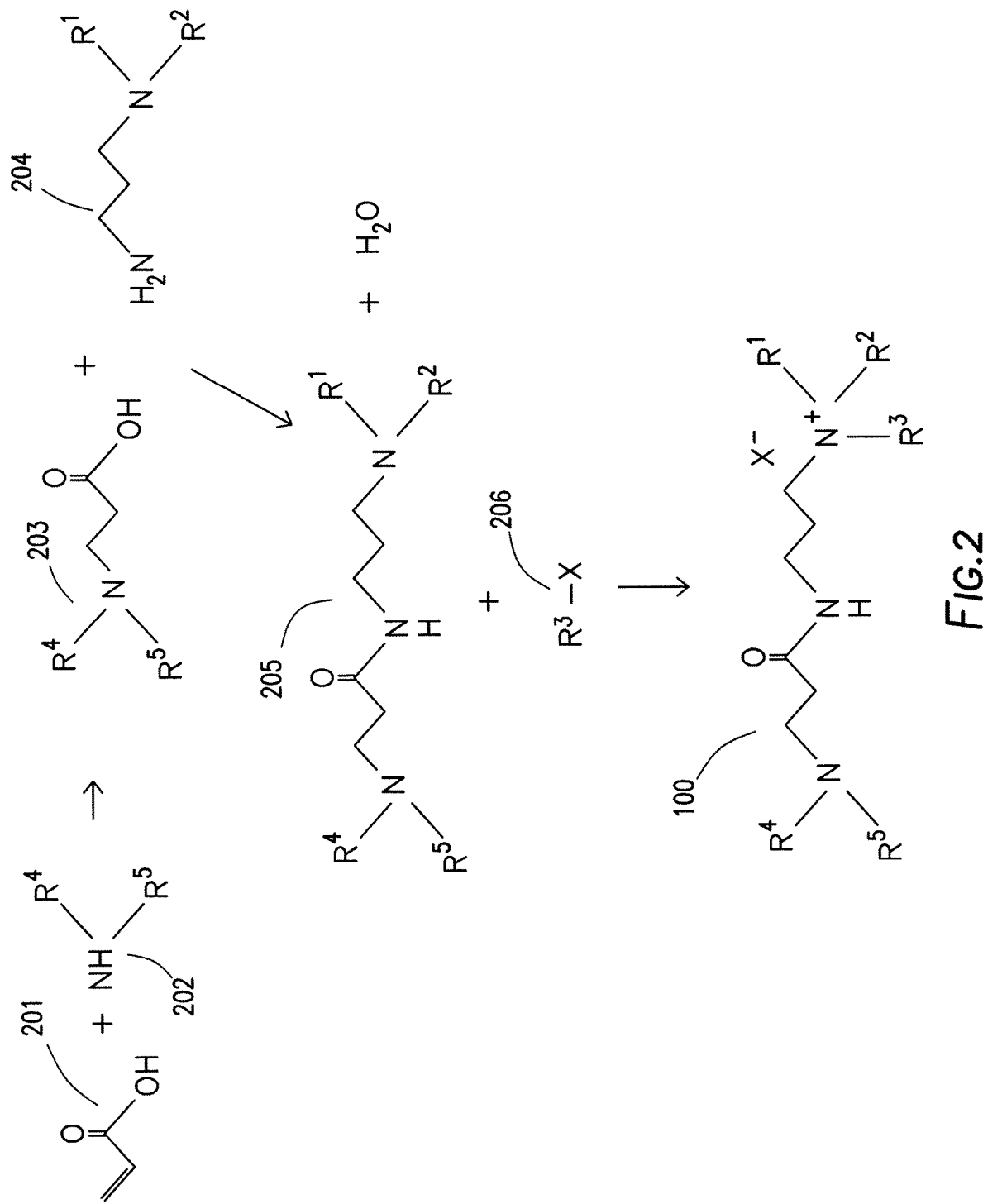
FIG. 2 is a diagram illustrating an example reaction process used to prepare a corrosion inhibitor additive in accordance with certain embodiments of the present disclosure.

FIG. 2 illustrates a potential reaction scheme for forming a corrosion inhibitor additive in accordance with certain embodiments. In the reaction scheme shown, acrylic acid 201 reacts with amine 202 (which, as shown in FIG. 2, includes hydrocarbon chains $R^4$ and $R^5$) to produce first intermediate 203. The first intermediate 203 in turn reacts with dialkylaminopropylamine 204 (which, as shown in FIG. 2, includes hydrocarbon chains $R^1$ and $R^2$) forming a second intermediate 205. The second intermediate 205 in turn reacts with alkylating agent 206 (which, as shown in FIG. 2, includes hydrocarbon chain $R^3$) to form compound 100. As can be seen, compound 100 includes two lipophilic tails $R^4$ and $R^5$ (retaining the hydrocarbon structures $R^4$ and $R^5$ of amine 202), a hydrophilic head 105 including R-groups $R^1$ and $R^2$ (retaining the hydrocarbon structure $R^1$ and $R^2$ of dialkylaminopropylamine 204) and R-group $R^3$ (retaining the hydrocarbon structure $R^3$ of alkylating agent 206), and a linking moiety including an amide group with an alkyl chain on each side of the amide group and an amino group connected to the lipophilic tails $R^4$ and $R^5$. Such reactions may, in some embodiments, take place within a range of about 80° C. to about 250° C. at approximately atmospheric pressure or lower. It will be appreciated by one of ordinary skill in the art having the benefit of the present disclosure that various modifications may be made to this reaction scheme to produce other corrosion inhibitor additives.

In certain embodiments, the corrosion inhibitor additives may be provided, used, and/or introduced as a salt. In such embodiments, the salt may include a counter anion. For example, the compound 100 as shown in FIGS. 1 and 2 includes a salt with a counter anion X. In certain embodiments, such salts may wholly or partially dissociate in aqueous solution. In other embodiments, the salts may remain substantially associated (either with the original anion or with other ions from solution). Counter anions suitable for one or more embodiments of the present disclosure may include, but are not limited to a carbonate, a carboxylate, a halide, a sulfate, an organic sulfonate, a hydroxide, a phosphate, a borate, and any combination thereof. It will be appreciated by one of ordinary skill in the art having the benefit of this disclosure that salts may be formed with other counter anions instead of or in addition to the counter anions specifically disclosed herein. In some embodiments, the counter anion $X^-$ is derived from an acid, including, but not limited to acetic acid, carboxylic acid, carbonic acid, methane sulfonic acid, sulfuric acid, sulfonic acid, boric acid, phosphoric acid, thioglycolic acid, and any combination or derivative thereof, for example.

In certain embodiments, the corrosion inhibitor additives may have substantially the following structural formula:

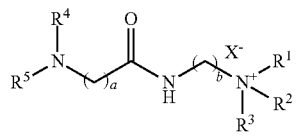

In such embodiments, each of $R^1$ and $R^2$ may independently be a $C_1$ to $C_{16}$ hydrocarbyl group according to the previous discussion of the $R^1$ and $R^2$ groups; $R^3$ may be selected from the group consisting of hydrogen and any $C_1$ to $C_{16}$ hydrocarbyl group according to the previous discussion of the $R^3$ group; $R^4$ may be selected from the group consisting of hydrogen and any $C_1$ to $C_{50}$ hydrocarbyl group according to the previous discussion of the $R^4$ group; $R^5$ may be a $C_1$ to $C_{50}$ hydrocarbyl group according to the previous discussion of the $R^5$ group; $X^-$ may be a counter anion according to the previous discussion; and each of a and b may be independently an integer from 1 to 10 according to the previous discussion of the alkyl chains of the linking moiety.

In certain embodiments, the corrosion inhibitor additive may be added to a fluid that comes into contact with a metal surface. In certain embodiments, one or more corrosion inhibitor additives may be introduced into a wellhead, a wellbore, a subterranean formation, a conduit, a vessel, and the like and may contact and/or be exposed to a metal surface residing therein. The corrosion inhibiting additives may be introduced in a subterranean formation and/or well bore in conjunction with one or more treatment fluids. As used herein, the term "treatment fluid" refers to any fluid that may be used in an application in conjunction with a desired function and/or for a desired purpose. The term "treatment" does not imply any particular action by the fluid or any component thereof. The treatment fluids generally include a base fluid. Treatment fluids that may be useful in accordance with the present disclosure include, but are not limited to, fracturing fluids, gravel packing fluids, pre-pad fluids, pad fluids, preflush fluids, afterflush fluids, acidic fluids, consolidation fluids, cementing fluids, wellbore clean-out fluids, conformance fluids, aqueous fluids (e.g, fresh water, salt water, brines, etc.), non-aqueous fluids (e.g., mineral oils, synthetic oils, esters, etc.), hydrocarbon-based fluids (e.g., kerosene, xylene, toluene, diesel, oils, etc.), foamed fluids (e.g., a liquid that includes a gas), gels, emulsions, gases, and the like. In one or more embodiments, the treatment fluid may have a pH within a range of from about 4 to about 8. In one or more embodiments, the treatment fluid may have a pH within a range of from about 5 to about 10. In other embodiments, the treatment fluid including the corrosion inhibitor additive may have a pH greater than 4, 5, 6, 7, 8, or 9.

The methods and compositions of the present disclosure may be used during or in conjunction with any subterranean operation. Suitable subterranean operations may include, but are not limited to, preflush treatments, afterflush treatments, drilling operations, hydraulic fracturing treatments, sand control treatments (e.g., gravel packing), acidizing treatments (e.g., matrix acidizing or fracture acidizing), "frac-pack" treatments, well bore clean-out treatments, and other operations where a treatment fluid or corrosion-inhibiting additive may be useful. In certain embodiments, the corrosion inhibitor additives may be used in near wellbore clean-out operations, wherein a treatment fluid may be circulated in the subterranean formation, thereby suspending or solubilizing particulates residing in the formation. The treatment fluid then may be recovered out of the formation, carrying the suspended or solubilized particulates with it. In certain embodiments, the methods and/or compositions of the present disclosure may be used in construction and/or operation of pipelines (e.g., transportation pipelines, distribution pipelines, etc.) or umbilical equipment that may be used, among other purposes, to transport various fluids (e.g., treatment fluids and/or fluids produced from subterranean formations).

In certain embodiments, the fluid including the corrosion inhibitor additive may be flowing or it may be substantially stationary. In certain embodiments, the fluid may be within a vessel, within a conduit (e.g., a conduit that may transport the fluid), within a subterranean formation, within a wellbore penetrating a portion of the subterranean formation, and/or within a wellhead of a wellbore. Examples of conduits suitable for certain embodiments include, but are not limited to pipelines, production piping, subsea tubulars, process equipment, and the like as used in industrial settings and/or as used in the production of oil and/or gas from a subterranean formation, and the like. In particular embodiments, the conduit may be a wellhead, a wellbore, or may be located within a wellbore penetrating at least a portion of a subterranean formation. Such oil and/or gas well may, for example, be a subsea well (e.g., with the subterranean formation being located below the sea floor), or it may be a surface well (e.g., with the subterranean formation being located belowground). A vessel or conduit according to other embodiments may be located in an industrial setting such as a refinery (e.g., separation vessels, dehydration units, pipelines, heat exchangers, and the like), or may be a transportation pipeline.

In some embodiments, the corrosion inhibitor additive may be incorporated into a fluid. For example, in some embodiments, the corrosion inhibitor additive may be added to a treatment fluid for use in a wellbore penetrating a subterranean formation during, for instance, oil and/or gas recovery operations. The fluid may include a solvent for the corrosion inhibitor additive. Solvents suitable for certain embodiments of the present disclosure include, but are not limited to methanol, isopropyl alcohol, glycol, ethylene glycol, toluene, xylene, monobutyl ether, hexane, cyclohexane, and any combination or derivative thereof, for example. In some embodiments, the solvent may be an alcohol. In certain embodiments, the solvent may be an organic solvent.

In one or more embodiments, one or more corrosion inhibitor additives may be introduced into and/or present in a fluid in an amount within a range of from about 25 ppm to about 500 ppm based on the volume of the fluid. In various embodiments, an effective amount of one or more corrosion inhibitor additives for inhibiting, retarding, mitigating, reducing, controlling, and/or delaying corrosion may be as low as any of: 25, 50, 75, 100, 125, 150, 175, 200, 225, 250, 275, 300, 325, 350, 375, 400, 425, 450, and 475 ppm based on the volume of the fluid. In certain embodiments, an effective amount of corrosion inhibitor additives in a fluid may be as high as any of: 50, 75, 100, 125, 150, 175, 200, 225, 250, 275, 300, 325, 350, 375, 400, 425, 450, 475, and 500 ppm based on the volume of the fluid. Thus, in one or more embodiments, an effective amount of corrosion inhibitor additives for inhibiting, retarding, mitigating, reducing, controlling, and/or delaying corrosion may be within a range of from about 10 to about 500 ppm based on the volume of the fluid; from about 25 to about 500 ppm by volume based on the volume of the fluid; from about 50 to about 500 ppm by volume based on the volume of the fluid; from about 25 to about 200 ppm by volume based on the volume of the fluid; from about 25 to about 350 ppm by volume based on the volume of the fluid; or from about 100 to about 300 ppm by volume based on the volume of the fluid. It further will be appreciated by one of ordinary skill in the art having the benefit of the present disclosure that the amount of the corrosion inhibitor additives effective for inhibiting, retarding, reducing, controlling, and/or delaying corrosion may depend upon, for example, the temperature, pressure, fluid composition, other additives in the fluid, and other conditions.

In certain embodiments, one or more corrosion inhibitor additives may be introduced to and/or contact any of various fluids having different water cuts (i.e., the ratio of the volume of water in the fluid to the total volume of the fluid). For example, in some embodiments the water cut of the fluid may be within a range of from about 1 to about 65%. In other embodiments, the water cut may be as low as any one of: 20, 25, 30, 35, 40, 45, 50, 55, 60, and 65%. In certain embodiments, the water cut may be as high as any one of: 35, 40, 45, 50, 55, 60, 65, 70, 75, 80, 85, 90, and 95%. In certain embodiments, a fluid may have a water cut of 30% or more, 35% or more, 40% or more, 45% or more, 50% or more, 55% or more, or 60% or more, up to about 99%. In other embodiments, one or more corrosion inhibitor additives may be introduced into or contact a fluid with any water cut within a range of from about 1% to about 99%.

In certain embodiments, the fluid to which one or more corrosion inhibitor additives may be introduced optionally may include any number of additives. Examples of such additives include, but are not limited to salts, surfactants, acids, proppant particulates, diverting agents, fluid loss control additives, nitrogen, carbon dioxide, surface modifying agents, tackifying agents, foamers, additional corrosion inhibitors, corrosion inhibitor intensifiers, scale inhibitors, hydrate inhibitors, catalysts, clay control agents, biocides, friction reducers, antifoam agents, bridging agents, flocculants, $H_2S$ scavengers, $CO_2$ scavengers, oxygen scavengers, lubricants, viscosifiers, breakers, weighting agents, relative permeability modifiers, resins, wetting agents, coating enhancement agents, filter cake removal agents, antifreeze agents (e.g., ethylene glycol), and the like. A person skilled in the art, with the benefit of this disclosure, will recognize the types of additives that may be included in the fluids for a particular application.

In certain embodiments, the corrosion inhibitor additives may be introduced into a wellhead of a wellbore penetrating at least a portion of the subterranean formation, a wellbore, a subterranean formation, a vessel, and/or a conduit (and/or into a fluid within any of the foregoing) using any method or equipment known in the art. In certain embodiments, the corrosion inhibitor additive is introduced into a wellbore penetrating at least a portion of a subterranean formation through which a fluid is flowing. For example, the corrosion inhibitor additives may be applied to a subterranean formation and/or wellbore using batch treatments, squeeze treatments, continuous treatments, and/or any combination thereof. In certain embodiments, a batch treatment may be performed in a subterranean formation by stopping production from the well and pumping the fluid including the corrosion inhibitor into a wellbore, which may be performed at one or more points in time during the life of a well. In other embodiments, a squeeze treatment may be performed by dissolving a corrosion inhibitor additive in a suitable solvent at a suitable concentration and squeezing that solvent carrying the corrosion inhibitor downhole into the formation, allowing production out of the formation to bring the corrosion inhibitor to its desired location.

In other embodiments, a corrosion inhibitor additive may be injected into a portion of a subterranean formation using an annular space or capillary injection system to continuously introduce the corrosion inhibitor additive into the formation. In certain embodiments, a composition (such as a treatment fluid) including a corrosion inhibitor additive may be circulated in the wellbore using the same types of pumping systems and equipment at the surface that are used to introduce treatment fluids or additives into a wellbore penetrating at least a portion of the subterranean formation. In certain embodiments, the corrosion inhibitor additive may be introduced to a fluid through a conduit or an injection point in fluid communication with a wellbore in which the fluid resides. In certain embodiments, the fluid is introduced through a conduit through which the fluid is flowing.

Figure 3:
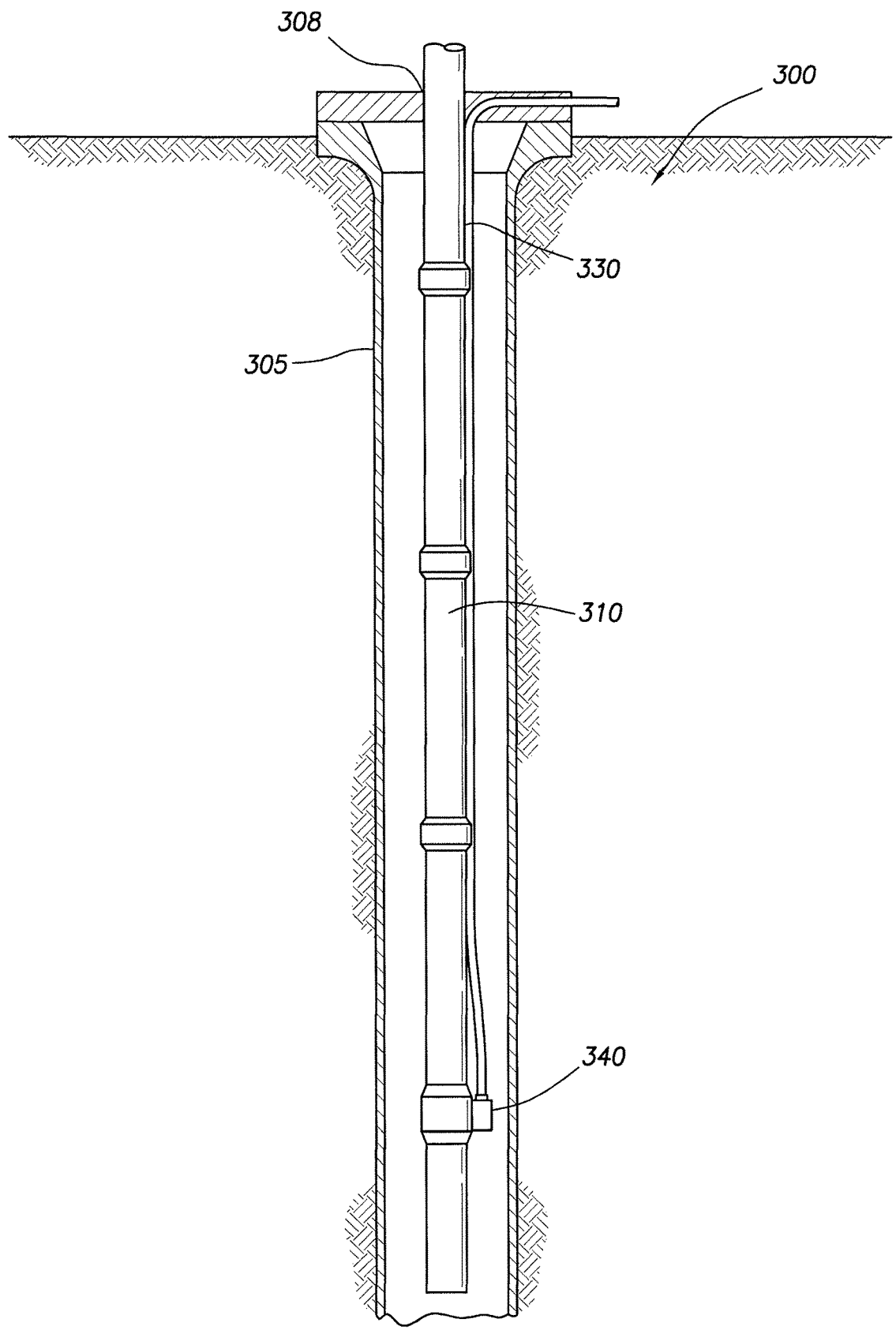
FIG. 3 is a diagram illustrating an injection system used in accordance with certain embodiments of the present disclosure.

For example, a corrosion inhibitor additive may be introduced into a wellbore and/or tubing using a capillary injection system as shown in FIG. 3. Referring now to FIG. 3, wellbore 305 has been drilled to penetrate a portion of a subterranean formation 300. A tubing 310 (e.g., production tubing) has been placed in the wellbore 305. A capillary injection tube 330 is disposed in the annular space between the outer surface of tubing 310 and the inner wall of wellbore 305. The capillary injection tube 330 is connected to a side-pocket mandrel 340 at a lower section of the tubing 310. A corrosion inhibitor additive may be injected into capillary injection tube 330 at the wellhead 308 at the surface such that it mixes with production fluid at or near the side-pocket mandrel 340. As the production fluid flows through the tubing 310, the corrosion inhibitor additive may prevent, inhibit, retard, reduce, control, and/or delay corrosion within the tubing 310. Other capillary injection systems and side pocket mandrel devices (e.g., those used in gas lift production) may be used in a similar manner to the system shown in FIG. 3.

In certain embodiments, a corrosion inhibitor additive may be added to a conduit such as a pipeline where one or more fluids enter the conduit and/or at one or more other locations along the length of the conduit. In such embodiments, the corrosion inhibitor additive may be added in batches or injected substantially continuously while the pipeline is being used, for example, to maintain the concentration of the corrosion inhibitor additive in the fluid at a certain amount (e.g., one or more of the concentrations referenced above). Once introduced into a fluid, subterranean formation, wellbore, pipeline, vessel, or other location, the corrosion inhibitor additive may inhibit, retard, reduce, control, and/or delay corrosion within the fluid, subterranean formation, wellbore, pipeline, vessel, or other location.

An embodiment of the present disclosure is a method comprising contacting a metal surface with a fluid comprising a corrosion inhibitor additive, wherein the corrosion inhibitor additive comprises at least one compound having the structural formula:

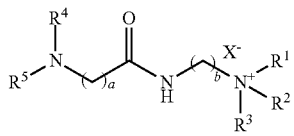

wherein each of $R^1$, $R^2$, and $R^3$ are independently selected from the group consisting of hydrogen and a $C_1$ to $C_{16}$ hydrocarbyl group, wherein $R^4$ is selected from the group consisting of hydrogen and a $C_1$ to $C_{50}$ hydrocarbyl group, wherein $R^5$ is a $C_1$ to $C_{50}$ hydrocarbyl group, wherein $X^-$ is a counter anion, and wherein each of a and b is independently an integer from 1 to 10.

In one or more embodiments described in the preceding paragraph, $X^-$ is selected from the group consisting of: a carboxylate, a halide, a sulfate, an organic sulfonate, a hydroxide, a phosphate, a borate, and any combination thereof. In one or more embodiments described above, the method further comprises the step of introducing the corrosion inhibitor additive to the fluid. In one or more embodiments described above, at least one of $R^1$, $R^2$, and $R^3$ comprise a heteroatom. In one or more embodiments described above, the metal surface comprises carbon steel. In one or more embodiments described above, the corrosion inhibitor additive is present in the fluid in an amount from about 25 ppm to about 500 ppm based on the volume of the fluid. In one or more embodiments described above, the fluid has a pH of from about 4 to about 10. In one or more embodiments described above, each of $R^4$ and $R^5$ is a $C_1$ to $C_{50}$ hydrocarbyl group resulting from a reaction between an acrylate or a methacrylate and an amine. In one or more embodiments described above, the amine is a synthetic primary or secondary amine selected from the group consisting of: butylamine, hexylamine, octylamine, dodecylamine, N-methyldodecylamine, N-methyloctylamine, didodecylamine, and any combination thereof. In one or more embodiments described above, the amine is a primary or secondary fatty amine derived from one or more fatty acids selected from the group consisting of: tallow, corn oil, canola oil, coconut oil, safflower oil, sesame oil, palm oil, cottonseed oil, soybean oil, olive oil, sunflower oil, hemp oil, wheat germ oil, palm kernel oil, vegetable oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof. In one or more embodiments described above, the compound is a reaction product of a reaction between (i) an alkylating agent or an acid and (ii) a second intermediate resulting from a reaction between a dialkylaminoalkylamine and a first intermediate, the first intermediate resulting from a reaction between an acrylate or a methacrylate and an amine.

Another embodiment of the present disclosure is a method comprising introducing a corrosion inhibitor additive into a wellbore penetrating at least a portion of a subterranean formation, wherein the corrosion inhibitor additive comprises at least one compound having the structural formula:

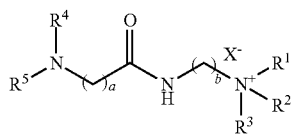

wherein each of $R^1$, $R^2$, and $R^3$ are independently selected from the group consisting of hydrogen and a $C_1$ to $C_{16}$ hydrocarbyl group, wherein $R^4$ is selected from the group consisting of hydrogen and a $C_1$ to $C_{50}$ hydrocarbyl group, wherein $R^5$ is a $C_1$ to $C_{50}$ hydrocarbyl group, wherein $X^-$ is a counter anion, and wherein each of a and b is independently an integer from 1 to 10; and contacting a metal surface in the wellbore with the corrosion inhibitor additive.

In one or more embodiments described in the preceding paragraph, the corrosion inhibitor additive is introduced into the wellbore through a conduit or an injection point in fluid communication with the wellbore. In one or more embodiments described above, $X^-$ is selected from the group consisting of: a carboxylate, a halide, a sulfate, an organic sulfonate, a hydroxide, a phosphate, a borate, and any combination thereof. In one or more embodiments described above, the metal surface comprises carbon steel. In one or more embodiments described above, the method further comprises allowing the corrosion inhibitor additive to contact a treatment fluid residing in the wellbore or subterranean formation. In one or more embodiments described above, at least one of $R^1$, $R^2$, and $R^3$ comprise a heteroatom. In one or more embodiments described above, $R^1$ is hydrogen, $R^2$ is a methyl group, $R^3$ is a methyl group, a is 2, b is 3, $R^4$ is hydrogen, $R^5$ is a $C_8$ to $C_{18}$ alkyl group, and $X^-$ is a carboxylate.

Another embodiment of the present disclosure is a method comprising: introducing a fluid comprising a corrosion inhibitor additive into at least a portion of a conduit or container comprising a metal surface, wherein the corrosion inhibitor additive comprises at least one compound having the structural formula:

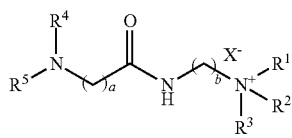

wherein each of $R^1$ and $R^2$ is independently a $C_1$ to $C_{16}$ hydrocarbyl group, wherein $R^3$ is selected from the group consisting of hydrogen and a $C_1$ to $C_{16}$ hydrocarbyl group, wherein $R^4$ is selected from the group consisting of hydrogen and a $C_1$ to $C_{50}$ hydrocarbyl group, wherein $R^5$ is a $C_1$ to $C_{50}$ hydrocarbyl group, wherein $X^-$ is a counter anion, and wherein each of a and b is independently an integer from 1 to 10; and contacting the metal surface with the corrosion inhibitor additive.

In one or more embodiments described in the preceding paragraph, $R^1$ is hydrogen, $R^2$ is a methyl group, $R^3$ is a methyl group, a is 2, b is 3, $R^4$ is hydrogen, $R^5$ is a $C_8$ to $C_{18}$ alkyl group, and $X^-$ is a carboxylate.

To facilitate a better understanding of the present disclosure, the following examples of certain aspects of certain embodiments are given. The following examples are not the only examples that could be given according to the present disclosure and are not intended to limit the scope of the disclosure or claims.

EXAMPLE

Figure 4:
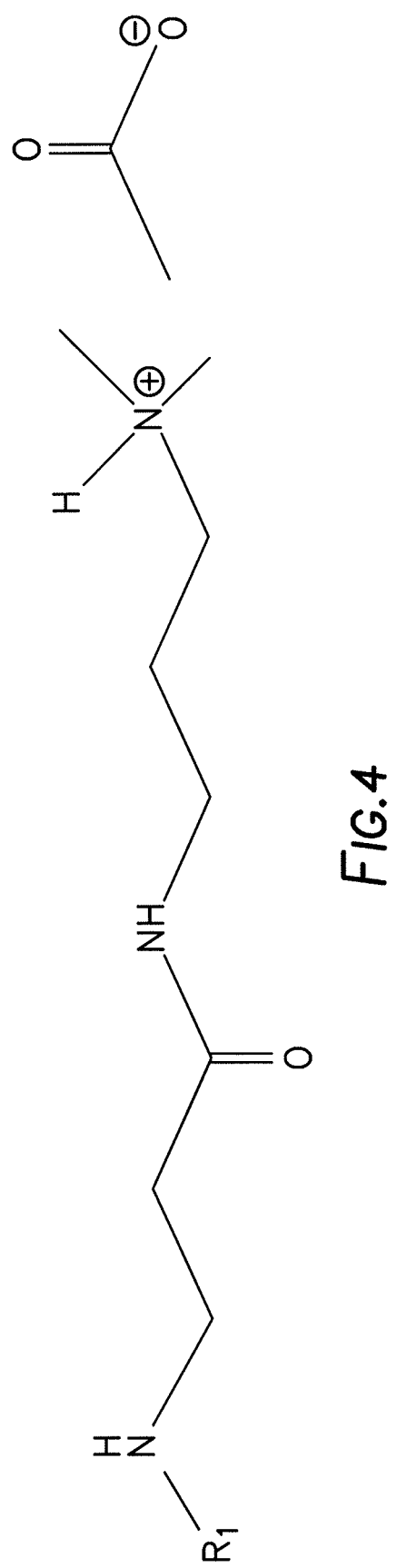
FIG. 4 is a diagram illustrating a corrosion inhibitor additive in accordance with certain embodiments of the present disclosure.
Figure 5:
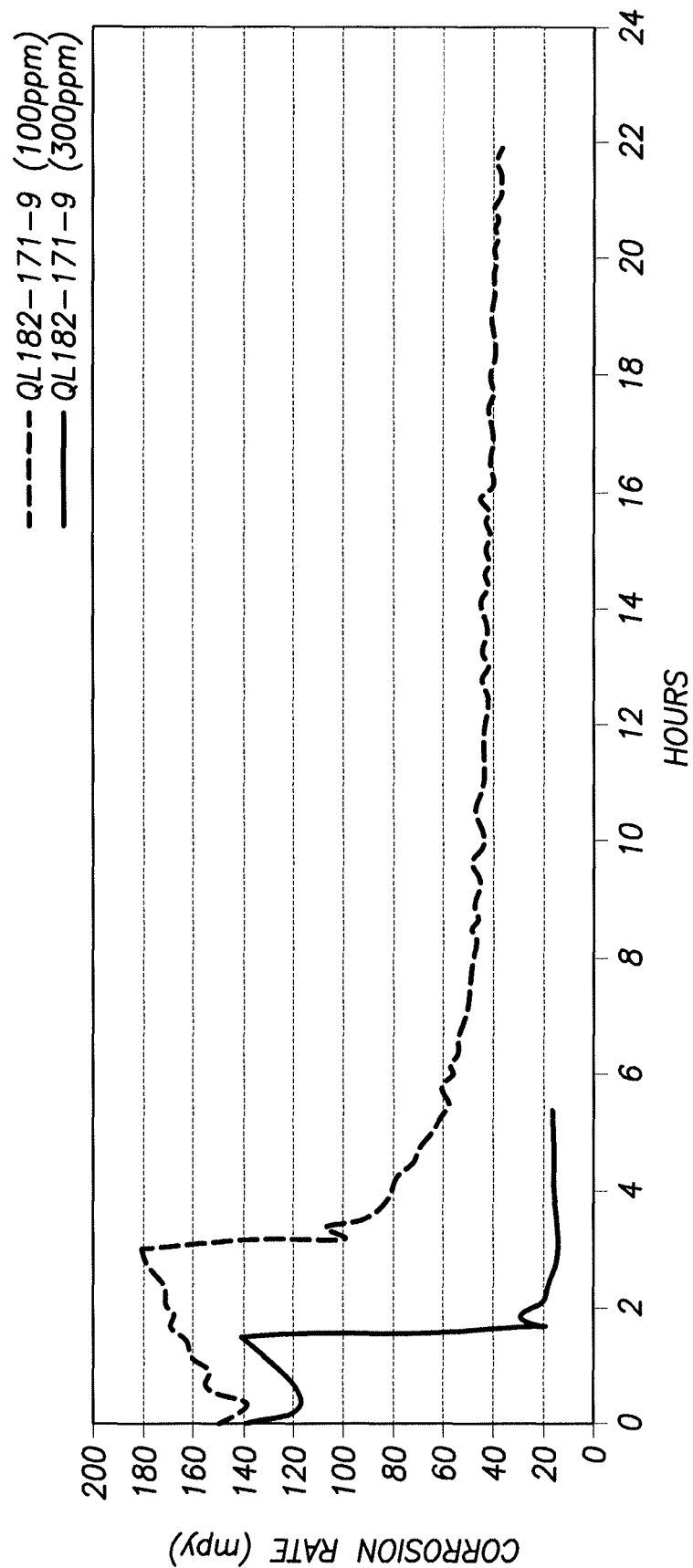
FIG. 5 is a graph illustrating data regarding corrosion rate versus time for the reaction kettle test of a corrosion inhibitor additive in accordance with certain embodiments of the present disclosure.

The corrosion inhibiting action of an example corrosion inhibitor additive of the present disclosure was evaluated using a linear polarization resistance technique and a Gamry electrochemical measurement system. A corrosion inhibitor additive including the compound of FIG. 4 where $R^1$ is a hydrocarbon group from a coco fatty amine, was formulated in two concentrations (100 ppm and 300 ppm) to test solutions that each included 800 mL synthetic sea-salt brine and 80 mL LVT-200 light petroleum distillate (available from various suppliers). The test solutions were heated to 150° F., continuously purged with $CO_2$, and stirred with a magnetic stir bar/plate combination. The corrosion inhibitor additives were added after approximately 1.5 hours. The working electrode (1018 carbon steel) was polarized+/−13 mV from its free corroding potential at a scan rate of 0.4 mV/second. The pseudo-reference electrode and counter electrode were 316SS rods. The corrosion rate on was measured using the linear polarization resistance technique, and those measurements are shown in FIG. 5. The average uninhibited corrosion rate (blank) was 158 mils per year (mpy) prior to injecting 100 ppm of the corrosion inhibitor additive. As shown in FIG. 5, the corrosion rate decreased to about 43 mpy about 12 hours after adding the corrosion inhibitor additive at 100 ppm. Accordingly, the corrosion inhibitor additive at 100 ppm provided 73% inhibition. When the dose rate was increased to 300 ppm of the corrosion inhibitor additive, the corrosion rate decreased to about 19 mpy after about 2 hours, a corrosion inhibition efficiency of 88%. These data demonstrate that the corrosion inhibitor additives of the present disclosure effectively inhibit corrosion at various concentrations.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:
1. A method comprising:
   contacting a metal surface with a fluid comprising a corrosion inhibitor additive, wherein the corrosion inhibitor additive comprises at least one compound having the structural formula:

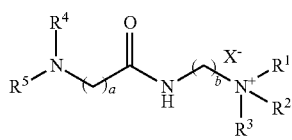

wherein each of $R^1$, $R^2$, and $R^3$ are independently selected from the group consisting of hydrogen and a $C_1$ to $C_{16}$ hydrocarbyl group, wherein $R^4$ is selected from the group consisting of hydrogen and a $C_1$ to $C_{50}$ hydrocarbyl group, wherein $R^5$ is a $C_1$ to $C_{50}$ hydrocarbyl group, wherein $X^-$ is a counter anion and wherein each of a and b is independently an integer from 1 to 10.

2. The method of claim 1, further comprising the step of introducing the corrosion inhibitor additive to the fluid.

3. The method of claim 1, wherein the metal surface comprises carbon steel.

4. The method of claim 1, wherein the corrosion inhibitor additive is present in an amount from about 25 ppm to about 500 ppm based on the volume of the fluid.

5. The method of claim 1, wherein the fluid has a pH of from about 4 to about 10.

6. The method of claim 1, wherein each of $R^4$ and $R^5$ is a $C_1$ to $C_{50}$ hydrocarbyl group resulting from a reaction between an acrylate or a methacrylate and an amine.

7. The method of claim 6, wherein the amine is a synthetic primary or secondary amine selected from the group consisting of: butylamine, hexylamine, octylamine, dodecylamine, N-methyldodecylamine, N-methyloctylamine, didodecylamine, and any combination thereof.

8. The method of claim 6, wherein the amine is a primary or secondary fatty amine derived from one or more fatty acids selected from the group consisting of: tallow, corn oil, canola oil, coconut oil, safflower oil, sesame oil, palm oil, cottonseed oil, soybean oil, olive oil, sunflower oil, hemp oil, wheat germ oil, palm kernel oil, vegetable oil, caprylic acid, capric acid, lauric acid, stearic acid, myristic acid, myristoleic acid, palmitic acid, palmitoleic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof.

9. The method of claim 1, wherein the compound is a reaction product of a reaction between (i) an alkylating agent or an acid and (ii) a second intermediate resulting from a reaction between a dialkylaminoalkylamine and a first intermediate, the first intermediate resulting from a reaction between an acrylate or a methacrylate and an amine.

10. A method comprising:
introducing a corrosion inhibitor additive into a wellbore penetrating at least a portion of a subterranean formation, wherein the corrosion inhibitor additive comprises at least one compound having the structural formula:

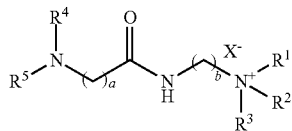

wherein each of $R^1$, $R^2$ and $R^3$ are independently selected from the group consisting of hydrogen and a $C_1$ to $C_{16}$ hydrocarbyl group, wherein $R^4$ is selected from the group consisting of hydrogen and a $C_1$ to $C_{50}$ hydrocarbyl group, wherein $R^5$ is a $C_1$ to $C_{50}$ hydrocarbyl group, wherein $X^-$ is a counter anion,, and wherein each of a and b is independently an integer from 1 to 10; and contacting a metal surface in the wellbore with the corrosion inhibitor additive.

11. The method of claim 10, wherein the corrosion inhibitor additive is introduced into the wellbore through a conduit or an injection point in fluid communication with the wellbore.

12. The method of claim 10, wherein the metal surface comprises carbon steel.

13. The method of claim 10, further comprising allowing the corrosion inhibitor additive to contact a treatment fluid residing in the wellbore or subterranean formation.

14. The method of claim 10, wherein $R^1$ is hydrogen, $R^2$ is a methyl group, $R^3$ is a methyl group, a is 2, b is 3, $R^4$ is hydrogen, and $R^5$ is a $C_8$ to $C_{18}$ alkyl group.

15. A method comprising:
introducing a fluid comprising a corrosion inhibitor additive into at least a portion of a conduit or container comprising a metal surface, wherein the corrosion inhibitor additive comprises at least one compound having the structural formula:

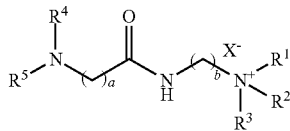

wherein each of $R^1$ and $R^2$ is independently a $C_1$ to $C_{16}$ hydrocarbyl group, wherein $R^3$ is selected from the group consisting of hydrogen and a $C_1$ to $C_{16}$ hydrocarbyl group, wherein $R^4$ is selected from the group consisting of hydrogen and a $C_1$ to $C_{50}$ hydrocarbyl group, wherein $R^5$ is a $C_1$ to $C_{50}$ hydrocarbyl group, wherein $X^-$ is a counter anion,, and wherein each of a and b is independently an integer from 1 to 10; and contacting the metal surface with the corrosion inhibitor additive.

16. The method of claim 15, wherein $R^1$ is hydrogen, $R^2$ is a methyl group, $R^3$ is a methyl group, a is 2, b is 3, $R^4$ is hydrogen, and $R^5$ is a $C_8$ to $C_{18}$ alkyl group.

17. The method of claim 1, wherein $X^-$ is selected from the group consisting of: a carboxylate, a halide, a sulfate, an organic sulfonate, a hydroxide, a phosphate, a borate, and any combination thereof.

18. The method of claim 1, wherein at least one of the $C_1$ to $C_{16}$ hydrocarbyl group of $R_1$, $R^2$, and $R^3$ comprises a heteroatom.

19. The method of claim 10, wherein $X^-$ is selected from the group consisting of:
a carboxylate, a halide, a sulfate, an organic sulfonate, a hydroxide, a phosphate, a borate, and any combination thereof.

* * * * *